United States Patent
Selders et al.

(10) Patent No.: US 12,076,462 B2
(45) Date of Patent: Sep. 3, 2024

(54) HYDRATABLE COMPOSITIONS COMPRISING MACROPARTICLES AND METHODS OF MAKING THEM

(71) Applicant: WARSAW ORTHOPEDIC, INC., Warsaw, IN (US)

(72) Inventors: Gretchen Selders, Memphis, TN (US); Ian Dunkley, Memphis, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 576 days.

(21) Appl. No.: 17/018,708

(22) Filed: Sep. 11, 2020

(65) Prior Publication Data

US 2021/0069382 A1    Mar. 11, 2021

Related U.S. Application Data

(60) Provisional application No. 62/898,924, filed on Sep. 11, 2019.

(51) Int. Cl.

| | | |
|---|---|---|
| *A61L 27/46* | (2006.01) | |
| *A61L 27/10* | (2006.01) | |
| *A61L 27/12* | (2006.01) | |
| *A61L 27/24* | (2006.01) | |
| *A61L 27/36* | (2006.01) | |
| *A61L 27/56* | (2006.01) | |

(52) U.S. Cl.
CPC .............. *A61L 27/46* (2013.01); *A61L 27/10* (2013.01); *A61L 27/12* (2013.01); *A61L 27/24* (2013.01); *A61L 27/3608* (2013.01); *A61L 27/362* (2013.01); *A61L 27/365* (2013.01); *A61L 27/56* (2013.01); *A61L 2400/06* (2013.01); *A61L 2430/02* (2013.01)

(58) Field of Classification Search
None
See application file for complete search history.

(56) References Cited

U.S. PATENT DOCUMENTS

| | | |
|---|---|---|
| 6,302,913 B1 | 10/2001 | Ripamonti et al. |
| 6,316,091 B1 | 11/2001 | Richart et al. |
| 7,842,300 B2 | 11/2010 | Atkinson et al. |
| 8,431,147 B2 | 4/2013 | Drapeau et al. |
| 8,486,080 B2 | 7/2013 | McKay |
| 8,653,029 B2 | 2/2014 | Vickers et al. |
| 8,926,552 B2 | 1/2015 | Walsh |
| 8,926,710 B2 | 1/2015 | McKay |
| 9,056,150 B2 | 1/2015 | Gross et al. |
| 8,968,323 B2 | 3/2015 | McKay |
| 9,034,358 B2 | 5/2015 | Behnam et al. |
| 9,308,190 B2 | 4/2016 | Li et al. |
| 2008/0031914 A1 | 2/2008 | Drapeau et al. |
| 2012/0116515 A1 | 5/2012 | Semler et al. |
| 2012/0310366 A1 | 12/2012 | To |
| 2014/0088618 A1 | 3/2014 | Song et al. |
| 2014/0161886 A1 | 6/2014 | Murphy et al. |
| 2014/0170202 A1 | 6/2014 | Peters et al. |
| 2014/0209501 A1 | 7/2014 | Govil et al. |
| 2016/0038646 A1 | 2/2016 | Bowlin et al. |
| 2016/0135954 A1 | 5/2016 | Schlachter et al. |
| 2016/0271296 A1 | 9/2016 | Jongpaiboonkit et al. |
| 2017/0333190 A1 | 11/2017 | Vickers et al. |
| 2021/0023258 A1 | 1/2021 | Dunkley et al. |
| 2021/0023263 A1 | 1/2021 | Dunkley et al. |
| 2021/0024430 A1 | 1/2021 | Dunkley et al. |
| 2022/0387663 A1 | 12/2022 | Dunkley et al. |

OTHER PUBLICATIONS

Daculsi, G., et al. "Smart Calcium Phosphate Bioceramic Scaffold for Bone Tissue Engineering," Key Engineering Materials. vols. 529-530: pp. 19-23 (Nov. 29, 2012) (Year: 2012).

Mastergraft Family of Products. webpage. Copyright Umg Uysal Medikal. Website visited Apr. 2022.

International Search Report and Written Opinion of the International Searching Authority (ISA/US) mailed Dec. 30, 2020 and issued in International Application No. PCT/US2020/050482 filed Sep. 11, 2020.

European Search Report. European Patent Office. Application No. 20862701.8-1109/4027949 PCT/US2020050482. 7 pgs. dtd May 17, 2023.

European Communication. European Patent Office. European Appl. No. 20 862 701.8-1109. dtd Mar. 26, 2024. 5 pgs.

*Primary Examiner* — David J Blanchard
*Assistant Examiner* — Daniel F Coughlin
(74) *Attorney, Agent, or Firm* — Sorell, Lenna & Schmidt, LLP

(57) ABSTRACT

A uniformly hydrated composition is provided and methods of making the uniformly hydrated composition. The method comprises providing a plurality of lyophilized porous macroparticles in a chamber, the plurality of lyophilized porous macroparticles each having an average diameter from about 0.1 mm to about 10 mm and comprising ceramic material and polymer; and mixing each of the plurality of lyophilized porous macroparticles with a fluid in the chamber to uniformly hydrate each of the plurality of lyophilized porous macroparticles to form a uniformly hydrated composition. Hydratable compositions are also provided.

16 Claims, 13 Drawing Sheets

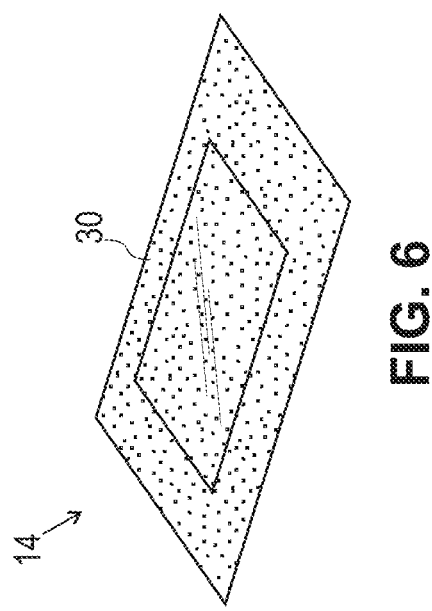
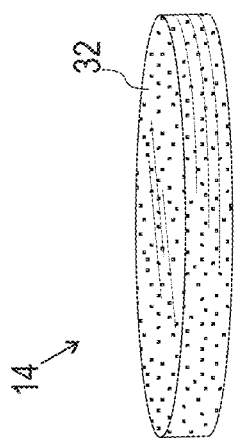
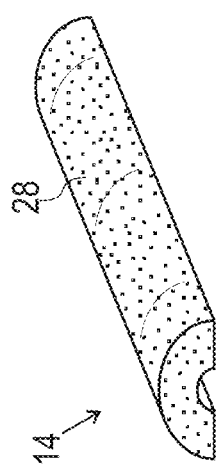
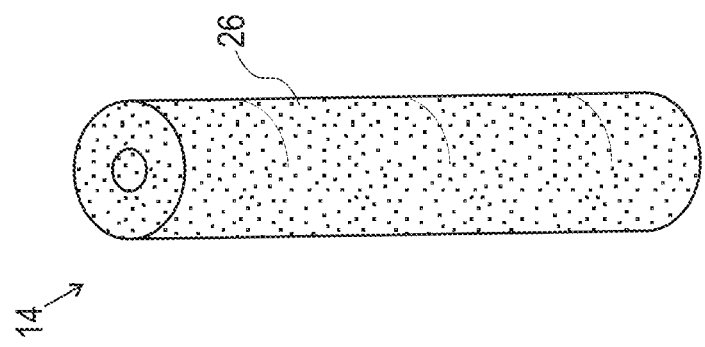
FIG. 6
FIG. 7
FIG. 5
FIG. 4

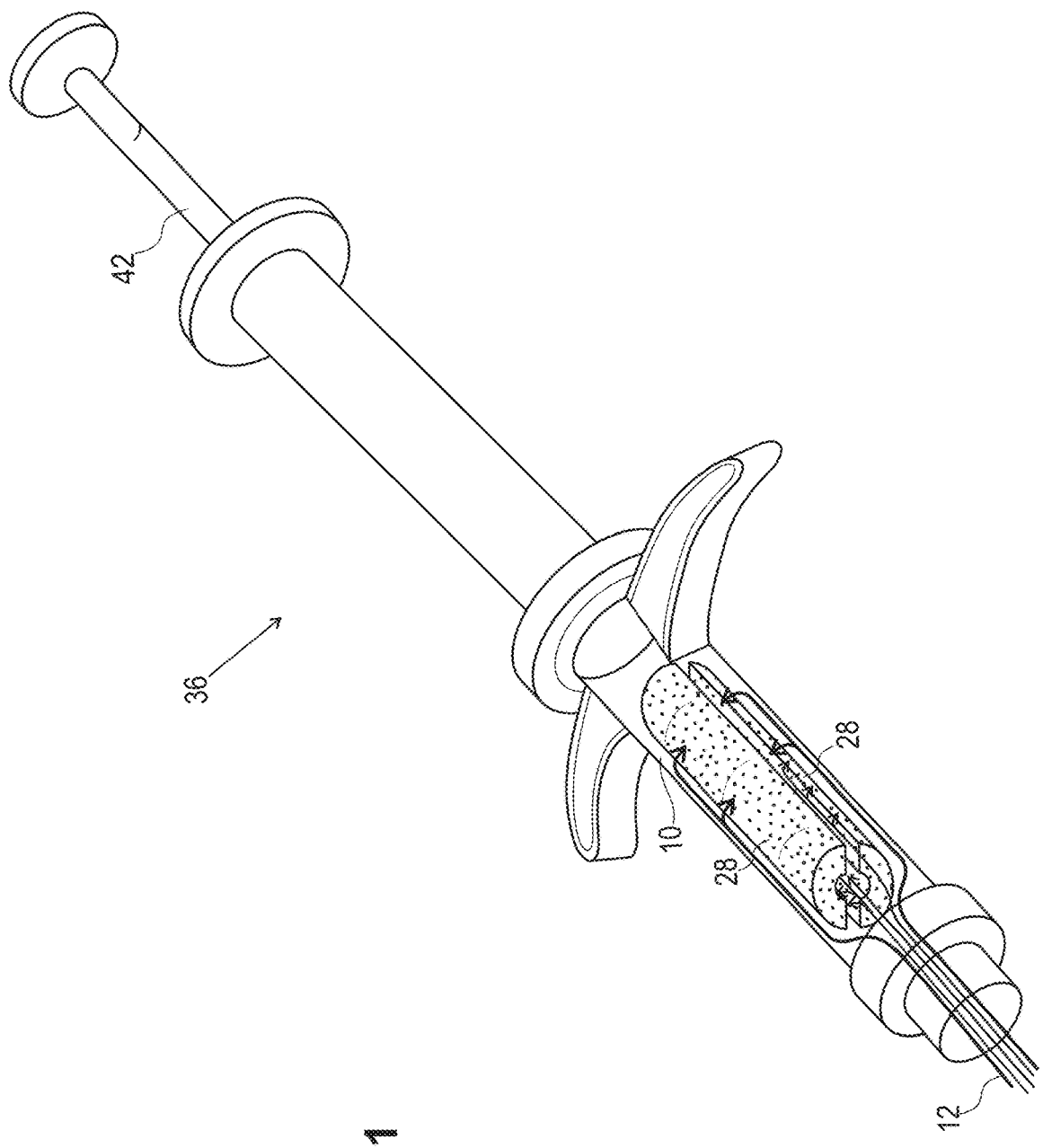
FIG. 11
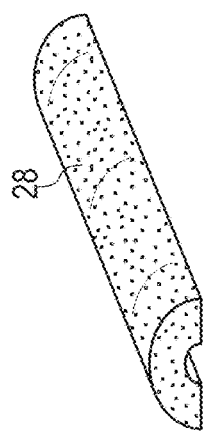

HYDRATABLE COMPOSITIONS COMPRISING MACROPARTICLES AND METHODS OF MAKING THEM

BACKGROUND

A variety of bone repair materials and bone void materials are used in the medical field. Among the known bone repair materials and bone void fillers used is autologous cancellous bone. This type of bone has the advantage of being both osteoinductive and non-immunogenic. Unfortunately, this type of bone is not available under all circumstances. Moreover, donor site morbidity and trauma add to the limitations of autologous cancellous bone.

Allograft bone is a reasonable bone graft substitute for autologous bone. It is readily available from cadavers and avoids the surgical complications and patient morbidity associated with harvesting autologous bone. Allograft bone is essentially a load-bearing matrix comprising cross-linked collagen, hydroxyapatite, and osteoinductive bone morphogenetic proteins (BMPs). Human allograft bone is widely used in orthopedic surgery. However, allograft bone does not always have the same strength properties or the cells and proteins that can influence the growth of new bone like autograft bone provides. Further, when using allograft bone, there is a slight chance of disease transmission and a lessened effectiveness since the bone growth cells and proteins are removed during the cleansing and disinfecting process.

An alternative to autograft and allograft bone is synthetic bone material, such as ceramic based bone material. Synthetic bone material can be administered in a syringe so that the bone material can be injected into a surgical site. However, often, when the synthetic bone material is hydrated with a fluid for administration, it can agglomerate and/or clump, making it difficult for the user to uniformly hydrate the synthetic bone material. Clumping of the material can cause the syringe to clog, making it more difficult to administer the synthetic bone material. Moreover, if the fluid does not uniformly mix with the synthetic bone material, excess fluid can be left in the syringe, and this fluid could be incorrectly administered into the surgical site.

Therefore, there is a need for a composition that can uniformly hydrate upon mixing with a fluid and that reduces unwanted separation of the fluid from the composition. There is also a need to provide a composition that is flowable and stable for administration.

SUMMARY

Methods and compositions are provided that comprise a composition that uniformly hydrates upon mixing with a fluid and that reduces unwanted separation of the fluid from the composition. The composition includes macroparticles that have a surface area that enhances hydration so that the composition uniformly hydrates and does not agglomerate during hydration. In some embodiments, a method of making a uniformly hydrated composition is provided. The method comprising providing a plurality of lyophilized porous macroparticles in a chamber, the plurality of lyophilized porous macroparticles each having an average diameter from about 0.1 mm to about 10 mm and comprising ceramic material and polymer; and mixing each of the plurality of lyophilized porous macroparticles with a fluid in the chamber to uniformly hydrate each of the plurality of lyophilized porous macroparticles to form a uniformly hydrated composition.

In some embodiments, a hydratable composition is provided. The composition comprises a plurality of lyophilized porous macroparticles comprising ceramic material in an amount from about 50 to about 98 wt. % and a polymer in an amount from about 2 to about 50 wt. % based on a total weight of each of the lyophilized porous macroparticles. Each of the lyophilized porous macroparticles have an average diameter from about 0.1 mm to about 10 mm. The plurality of lyophilized porous macroparticles are configured to hydrate with a fluid to form a uniformly hydrated composition.

In some embodiments, a hydratable composition is provided. The composition comprises a plurality of lyophilized porous macroparticles comprising porous ceramic granules having an average diameter from about 50 μm to 800 μm and in an amount from about 50 to about 98 wt. % and collagen in an amount from about 2 to about 50 wt. % based on a total weight of each of the lyophilized porous macroparticles. Each of the lyophilized porous macroparticles have an average diameter from about 0.1 mm to about 10 mm. The plurality of lyophilized porous macroparticles are configured to hydrate with a fluid to form a uniformly hydrated composition.

While multiple embodiments are disclosed, still other embodiments of the present application will become apparent to those skilled in the art from the following detailed description, which is to be read in connection with the accompanying drawings. As will be apparent, the present disclosure is capable of modifications in various obvious aspects, all without departing from the spirit and scope of the present disclosure. Accordingly, the detailed description is to be regarded as illustrative in nature and not restrictive.

BRIEF DESCRIPTION OF THE DRAWINGS

In part, other aspects, features, benefits and advantages of the embodiments will be apparent regarding the following description, appended claims and accompanying drawings.

FIG. 4 is a perspective view of one embodiment of a lyophilized porous macroparticle shaped as a single hollow tube.

FIG. 5 is a perspective view of one embodiment of a lyophilized porous macroparticle shaped as a half or hemisphere of a single hollow tube.

FIG. 6 is a perspective view of one embodiment of a lyophilized porous macroparticle shaped as a single rectangle.

FIG. 7 is a perspective view of one embodiment of a lyophilized porous macroparticle shaped as a single disc.

FIG. 11 is a perspective view of a plurality of lyophilized porous macroparticles shaped as two halves or hemispheres of a hollow tube loaded into a chamber of a syringe. Fluid is added to the syringe and the fluid flows concentrically from both internal and external sides.

In FIG. 13, a needle of a syringe is alternatively fenestrated to increase the speed of hydration of the macroparticles.

Figure 3:
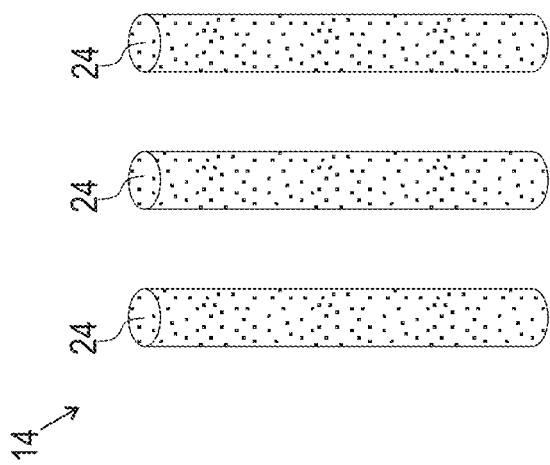
FIG. 3 is a perspective view of one embodiment of a plurality of lyophilized porous macroparticles shaped as rods or tubes.
Figure 2:
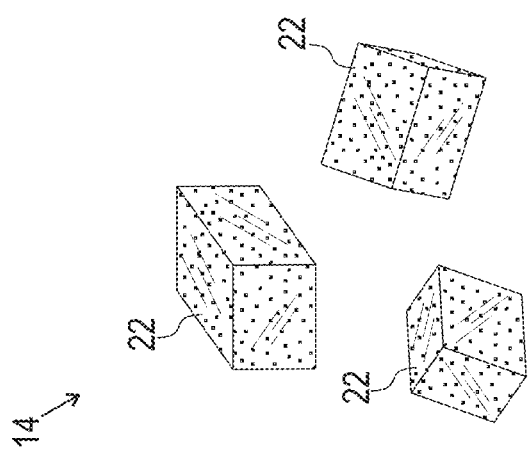
FIG. 2 is a perspective view of one embodiment of a plurality of lyophilized porous macroparticles shaped as cubes.

It is to be understood that the figures are not drawn to scale. Further, the relation between objects in a figure may not be to scale and may in fact have a reverse relationship as to size. The figures are intended to bring understanding and clarity to the structure of each object shown, and thus, some features may be exaggerated in order to illustrate a specific feature of a structure.

DETAILED DESCRIPTION

Definitions

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Similarly, when values are expressed as approximations, by use of the antecedent "about," it will be understood that the particular value forms another embodiment that is +/−10% of the recited value. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value.

Notwithstanding that the numerical ranges and parameters setting forth the broad scope of this application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Biocompatible, as used herein, is intended to describe materials that, upon administration in vivo, do not induce undesirable long-term effects.

Bone, as used herein, refers to bone that is cortical, cancellous or cortico-cancellous of autogenous, allogenic, xenogenic, or transgenic origin.

The term "autograft" refers to graft material harvested from the same individual patient who is also recipient of the graft, obtained surgically from non-essential donation sites in the patient.

Bone graft, as used herein, refers to any implant prepared in accordance with the embodiments described herein and therefore may include expressions such as a bone void filler.

The term "osteoinductive," as used herein, refers to the quality of being able to recruit cells from the host that have the potential to stimulate new bone formation. Any material that can induce the formation of ectopic bone in the soft tissue of an animal is considered osteoinductive.

The term "osteoinduction" refers to the ability to stimulate the proliferation and differentiation of pluripotent mesenchymal stem cells (MSCs). In endochondral bone formation, stem cells differentiate into chondroblasts and chondrocytes, laying down a cartilaginous ECM, which subsequently calcifies and is remodeled into lamellar bone. In intramembranous bone formation, the stem cells differentiate directly into osteoblasts, which form bone through direct mechanisms. Osteoinduction can be stimulated by osteogenic growth factors, although some ECM proteins can also drive progenitor cells toward the osteogenic phenotype.

The term "osteogenic" refers to the ability of a graft material to produce bone independently. To have direct osteogenic activity, the graft must contain cellular components that directly induce bone formation. For example, an allograft seeded with activated MSCs would have the potential to induce bone formation directly, without recruitment and activation of host MSC populations. Because many osteoconductive allografts also have the ability to bind and deliver bioactive molecules, their osteoinductive potential will be greatly enhanced.

The term "patient" refers to a biological system to which a treatment can be administered. A biological system can include, for example, an individual cell, a set of cells (e.g., a cell culture), an organ, or a tissue. Additionally, the term "patient" can refer to animals, including, without limitation, humans.

The term "implantable" as utilized herein refers to a biocompatible device (e.g., the composition) retaining potential for successful placement within a mammal. The expression "implantable composition" and expressions of the like as utilized herein refer to an object implantable through surgery, injection, or other suitable means whose primary function is achieved either through its physical presence or mechanical properties. An example of the implantable device is the composition.

The term "moldable" includes that the composition can be shaped by hand or machine or injected into the target tissue site (e.g., bone defect, fracture, or void) into a wide variety of configurations to fit within the bone defect.

The term "cohesive" as used herein means that the composition tends to remain a singular, connected mass upon the addition of fluid, autograft bone or during manipulation, including the exhibition of the ability to be molded shaped without breaking upon manipulating, or disintegrating or becoming unstable.

The terms "macroparticle" or "macroform" include bone material that is visible to the naked eye. The bone material can be natural bone, synthetic bone material (e.g., demineralized bone, ceramic, etc.) or a combination thereof that is solid or semi-solid before hydration. Typically, the macroparticle can be from 0.01 mm to about 50 mm in length. It is to be understood that the terms macroparticle and macroform can be used interchangeably.

The term "flowable" includes that the composition can be administered in an injectable state via a syringe and/or cannula. The composition is flowable when its consistency is fluid-like and has a viscosity that is lower than that of the viscosity of the composition when in a putty or paste form. Flowable compositions include liquid or fluid (e.g., solution, suspension, or the like) or semi-solid compositions (e.g., gels, cements) that are easy to manipulate and may be brushed, sprayed, dripped, injected, shaped and/or molded at or near the target tissue site. "Flowable" includes compositions with a low viscosity or water-like consistency to those with a high viscosity, such as a paste-like material. In various embodiments, the flowability of the composition allows it to conform to irregularities, crevices, cracks, and/or voids in the bone defect site (e.g., bone void). For example, in various embodiments, the composition may be used to fill one or more voids in an osteolytic lesion.

The term "injectable" refers to a mode of administering the composition. The composition can be administered in a variety of ways such as, for example, a syringe and/or cannula. For example, the composition can be administered parenterally, such as for example, anterior lumbar interbody administration for fusion, or posterior lumbar interbody administration for fusion or transforaminal lumbar interbody administration for fusion, other intraspinal injection or other local administration.

The term "hydrate," "hydration," "hydratable," "hydrating' or "hydrated" refers to adding an amount of fluid to a composition to increase the amount of moisture content in the composition to form a putty or paste that is flowable.

The term "dehydrated" or "dehydration" refers to a composition that contains a small amount of residual moisture or no moisture content and can be in the form of a dry composition. The dehydrated composition can have a moisture content from about 0 to about 10% based on the total weight of the composition. In some embodiments, when a composition is dehydrated, fluid can be added to the composition to hydrate the composition. A dehydrated composition includes a lyophilized or freeze-dried composition.

The term "bone marrow aspirate" or "BMA" refers to the withdrawal of bone marrow fluid through a syringe and needle to harvest the bone marrow fluid from the patient. Bone marrow aspirate comprises fluid that contains a heterogeneous mix of stem and progenitor cells, platelets and white blood cells. The bone marrow aspirate can be harvested from various sources in the body, including, but not limited to the iliac crest.

The term "soluble collagen" refers to the solubility of individual tropocollagen molecules in acidic aqueous environments. Tropocollagen may be considered the monomeric unit of collagen fibers and its triple helix structure is well recognized.

"Insoluble collagen" as used herein refers to collagen that cannot be dissolved in an aqueous alkaline or in an inorganic salt solution without chemical modification, and includes for example hides, splits and other mammalian or reptilian coverings. For example, "natural insoluble collagen" can be derived from the corium, which is the intermediate layer of an animal hide (e. g. bovine, porcine, fish, etc.) that is situated between the grain and the flesh sides.

The term "electrospun" or "electrospinning" as used herein, refers to a fiber production method which uses electric force to draw charged threads of polymer solutions or polymer melts up to fiber diameters in the order of microns to some hundred nanometers.

Compositions

As shown in FIGS. 1-16, a hydratable composition 10 is provided. The composition can be a bone graft material and is configured to uniformly hydrate when mixed with a fluid 12. The composition is configured to reduce unwanted separation of the fluid from the composition and will not agglomerate or clump when hydrated. In its final form, the composition can be a flowable putty, cement or gel.

The hydratable composition includes a plurality of lyophilized porous macroparticles 14 that are configured to hydrate with the fluid to form a uniformly hydrated composition. The plurality of lyophilized porous macroparticles comprise a ceramic material in an amount from about 50 to about 98 wt. % and a polymer in an amount from about 2 to about 50 wt. % based on a total weight of each of the lyophilized porous macroparticles. The plurality of lyophilized porous macroparticles can each include from about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97 to about 98 wt. % ceramic material and from about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 to about 50 wt. % polymer based on the total weight of each of the lyophilized porous macroparticles.

The polymer component of each of the plurality of lyophilized porous macroparticles can be porcine or bovine collagen, bovine type I collagen, tendon or dermis derived collagen or a combination thereof.

The ceramic material can comprise hydroxyapatite and beta-tricalcium phosphate having a calcium to phosphate ratio of between 1.0 to about 2.0. In some embodiments, the calcium to phosphate ratio is between 1.0, 1.1, 1.2, 1.3, 1.4, 1.5, 1.6, 1.7, 1.8, 1.9 to about 2.0.

The hydroxyapatite is in an amount of about 8 to about 22 wt. % based on a total weight of the ceramic material. The hydroxyapatite can be in a range from about 8, 9, 10, 11, 12, 13, 14, 15, 16, 17, 18, 19, 20, 21 to about 22 wt. %. In some embodiments, the hydroxyapatite can be in a range from about 1 to about 99 wt. %, such as from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 to about 99 wt. %.

The beta-tricalcium phosphate is in an amount of about 78 to about 92 wt. % based on a total weight of the ceramic material. The beta-tricalcium phosphate can be in an amount from about 78, 79, 80, 81, 82, 83, 84, 85, 86, 87, 88, 89, 90, 91 to about 92 wt. %. In some embodiments, the beta-tricalcium phosphate can be in a range from about 1 to about 99 wt. %, such as from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 to about 99 wt. %.

Each of the lyophilized porous macroparticles have an average diameter from about 0.1 mm to about 10 mm. For example, each of the lyophilized porous macroparticles can have an average diameter from about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9 to about 10 mm.

Each of the lyophilized porous macroparticles can have an average height and/or length from about 0.01 mm to about 10 mm or from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9 to about 10 mm.

Figure 15A:
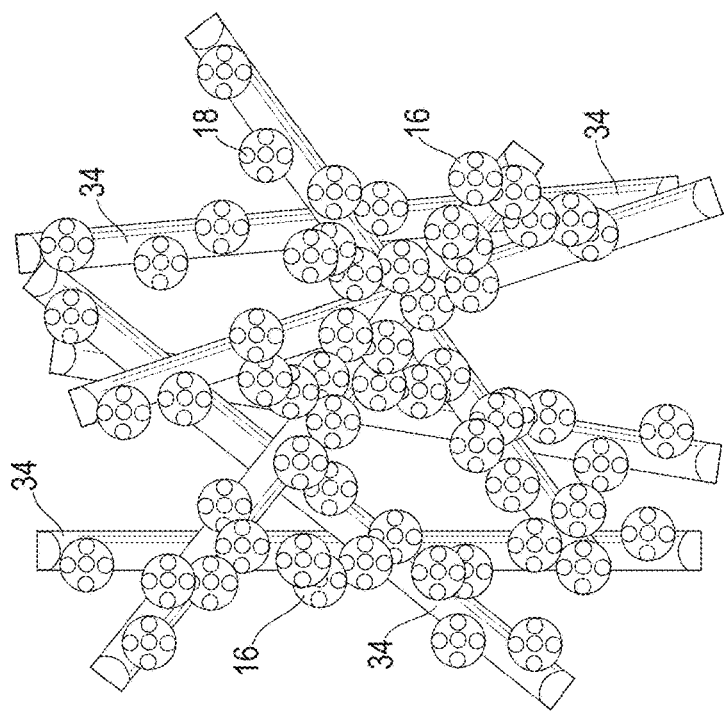
FIG. 15A is an enlarged perspective view of the electrospun fibers of FIG. 15.

The ceramic material provided in each of the lyophilized porous macroparticles can be in the form of porous ceramic granules 16, as show in FIG. 15A. The porous ceramic granules are similar to the granules found and described in U.S. application Ser. No. 16/523,259, filed on Jul. 26, 2019, assigned to Warsaw Orthopedic, Inc., which is incorporated herein by reference. The porous ceramic granules have an average diameter from about 50 µm to 800 µm. In some embodiments, the average diameter of the granules may be from about 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795 to about 800 µm. It is to be understood that the ceramic material is smaller in size than the macroparticles.

When the porous ceramic granules are used in the composition, the granules are in an amount from about 50 to about 98 wt. % and the collagen is in an amount from about 2 to about 50 wt. % based on a total weight of each of the lyophilized porous macroparticles. Each of the porous ceramic granules comprise hydroxyapatite and beta-tricalcium phosphate having a calcium to phosphate ratio of between 1.0 to about 2.0, as described above with regard to the ceramic material.

Each of the porous ceramic granules comprise an outer surface comprising a plurality of concave shapes 18, as shown in FIG. 15A. The concave shapes can be disc like in appearance and can be a particular size. The concave shapes can each have a diameter from about 400 to about 600 microns. In some embodiments, each diameter can be from about 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595 to about 600 microns.

The concave shapes on the outer surface of each granule can facilitate an increase in new bone attachment since the surface makes new bone attachment easier (e.g., vascularization and penetration of associated cells) than attachment would be on a standard ceramic granule. In some embodiments, the porous ceramic granules facilitate rapid and homogeneous osseointegration which supports bone healing by acting as a scaffold over which bone can grow.

Each of the porous ceramic granules have a Brunauer-Emmett-Teller (BET) surface area from about 0.2 to about 10 $m^2/g$. The BET surface area can be from about 0.2, 0.3, 0.4, 0.5, 0.6, 0.7, 0.8, 0.9, 1, 2, 3, 4, 5, 6, 7, 8, 9 to about 10 $m^2/g$. The increase in surface area further facilitates new bone growth by allowing the granules to dissolve and release calcium faster than a regular granule would.

Each of the porous ceramic granules can have a microporosity, and the diameter of the micropores is from about 0.01 to about 10 microns. In some embodiments, the diameter of each of the micropores can be from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9 to about 10 microns.

The plurality of lyophilized porous macroparticles can be made into a variety of shapes after lyophilization or through the use of cryogel applications. The shapes can be cut from a textured or flat shaped sheet of bone material comprising the ceramic material and polymer or can be prepared as individual macroparticles created in molds. The macroparticles are porous, but in some embodiments, the macroparticles are highly porous. For example, porous macroparticles can include that the macroparticles have a porosity from about 10 to about 80% or from about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 to about 80%. Highly porous macroparticles can include that the macroparticles have a porosity from about 81 to about 99% or from about 81, 82, 83, 84, 85, 86, 87, 88, 89, 90, 91, 92, 93, 94, 95, 96, 97, 98 to about 99%.

Figure 1:
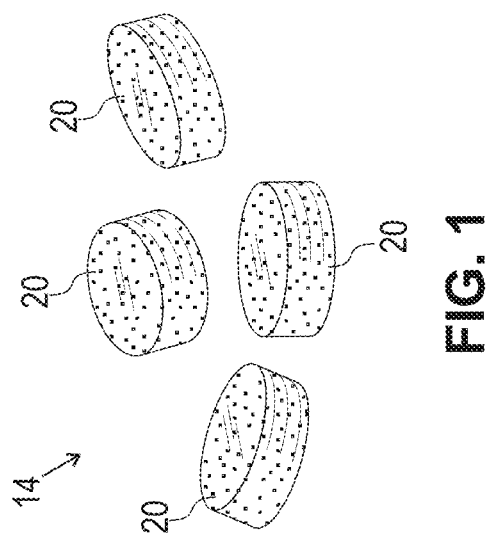
FIG. 1 is a perspective view of one embodiment of a plurality of lyophilized porous macroparticles shaped as cylinders.
Figure 26:
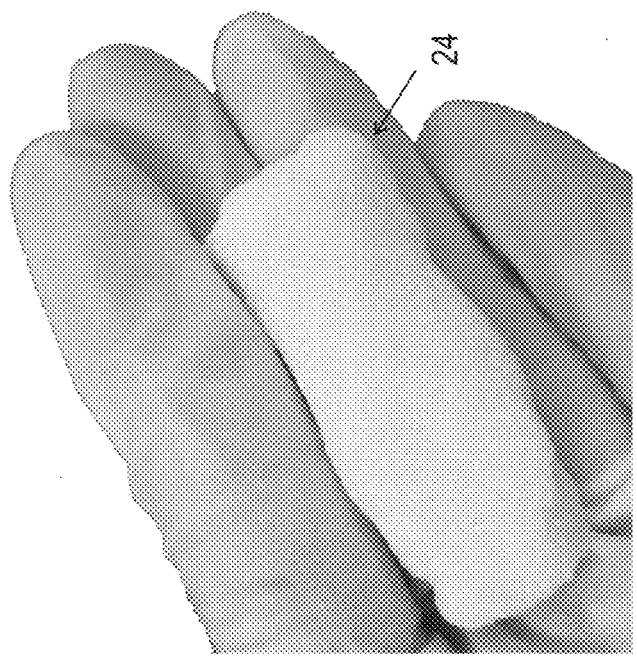
FIG. 26 illustrates lyophilized porous macroparticles that were hydrated with water and molded by hand into a tubular shape.

The macroparticle shapes and size create a high level of surface area which increases uniform hydration when fluid is administered to the macroparticles. For example, due to the high level of surface area, fluid will rapidly move into the macroparticles through wicking. The macroparticle shapes can include cylinders 20, as shown in FIG. 1; cubes 22, as shown in FIG. 2 and FIGS. 23-25; rods or tubes 24, as shown in FIG. 3 and FIG. 26; a hollow tube or tubes 26, as shown in FIG. 4; a half hemispherical hollow tube or tubes 28, as shown in FIG. 5; a rectangle or rectangles 30, as shown in FIG. 6; a disc or discs 32, as shown in FIG. 7; electrospun fibers 34, as shown in FIG. 15 or a combination thereof.

The plurality of lyophilized porous macroparticles can be loaded into a barrel or chamber 38 of a syringe 36. The plurality of lyophilized porous macroparticles in the chamber can have a packing density to maximize hydration of the plurality of lyophilized porous macroparticles when fluid is introduced into the chamber. In some embodiments, the packing density can be high. The packing density can be from about 1 to about 5 g/cm$^3$, from about 1 to about 4 g/cm$^3$, from about 1 to about 3 g/cm$^3$, or from about 1 to about 2 g/cm$^3$. The packing density can be from about 1, 2, 3, 4 to about 5 g/cm$^3$. In some embodiments, the packing density of the macroparticles combined with the high surface area of the macroparticles, creates a uniformly hydrated composition that does not agglomerate and is flowable.

Figure 8:
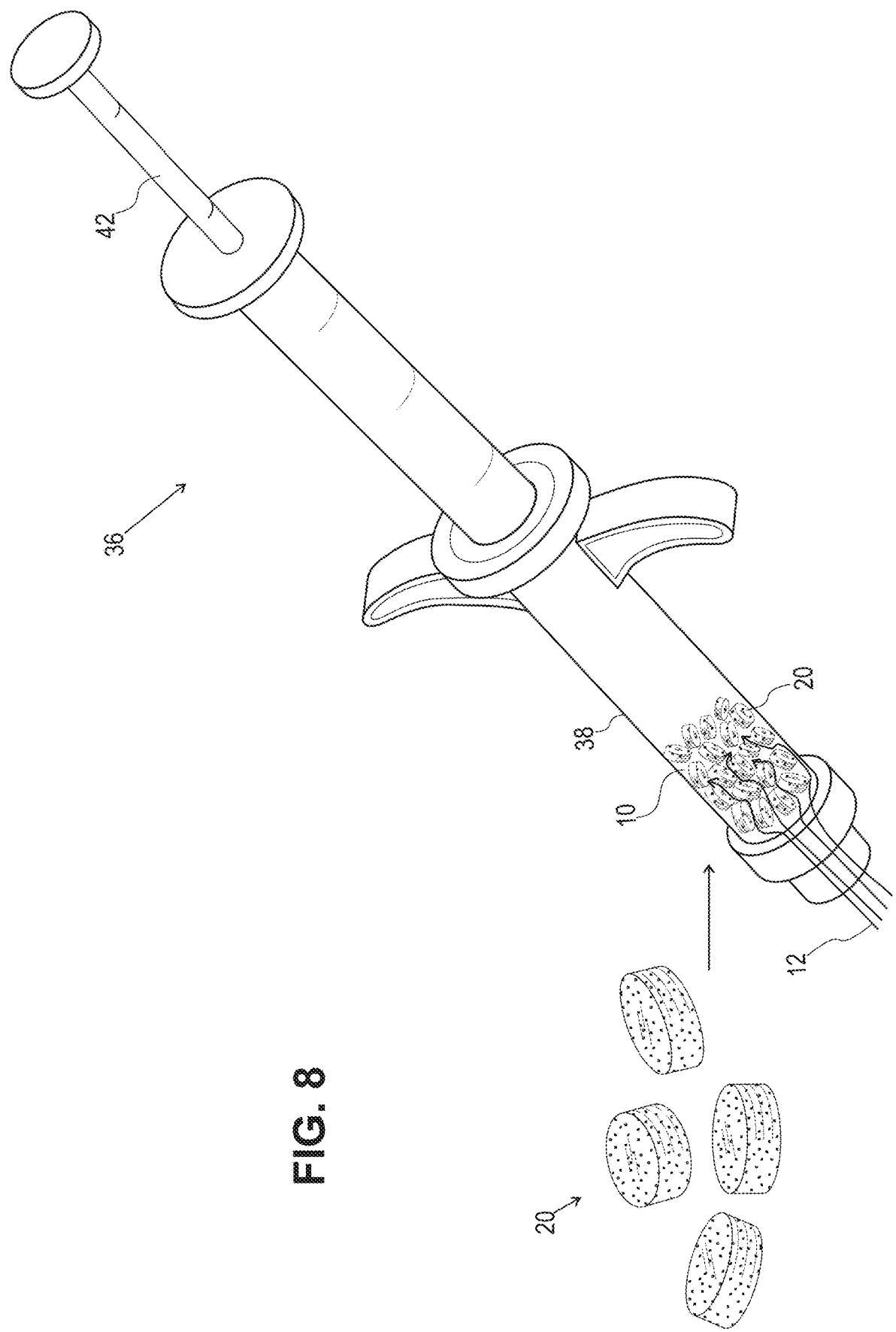
FIG. 8 is a perspective view of a plurality of lyophilized porous macroparticles shaped as cylinders loaded into a chamber of a syringe. Fluid is added to the syringe and the fluid moves around the plurality of lyophilized porous macroparticles uniformly.

FIGS. 8-11 illustrate how the macroparticles of the composition facilitate uniform hydration. FIG. 8 shows the cylindrically shaped macroparticles of FIG. 1 loaded into the chamber of the syringe. Fluid is added to the syringe and the fluid will move around each of the macroparticles creating uniform hydration. The fluid can fill the spaces or voids that surround each of the macroparticles loaded in the chamber and can also wick into each of the macroparticles.

Figure 9:
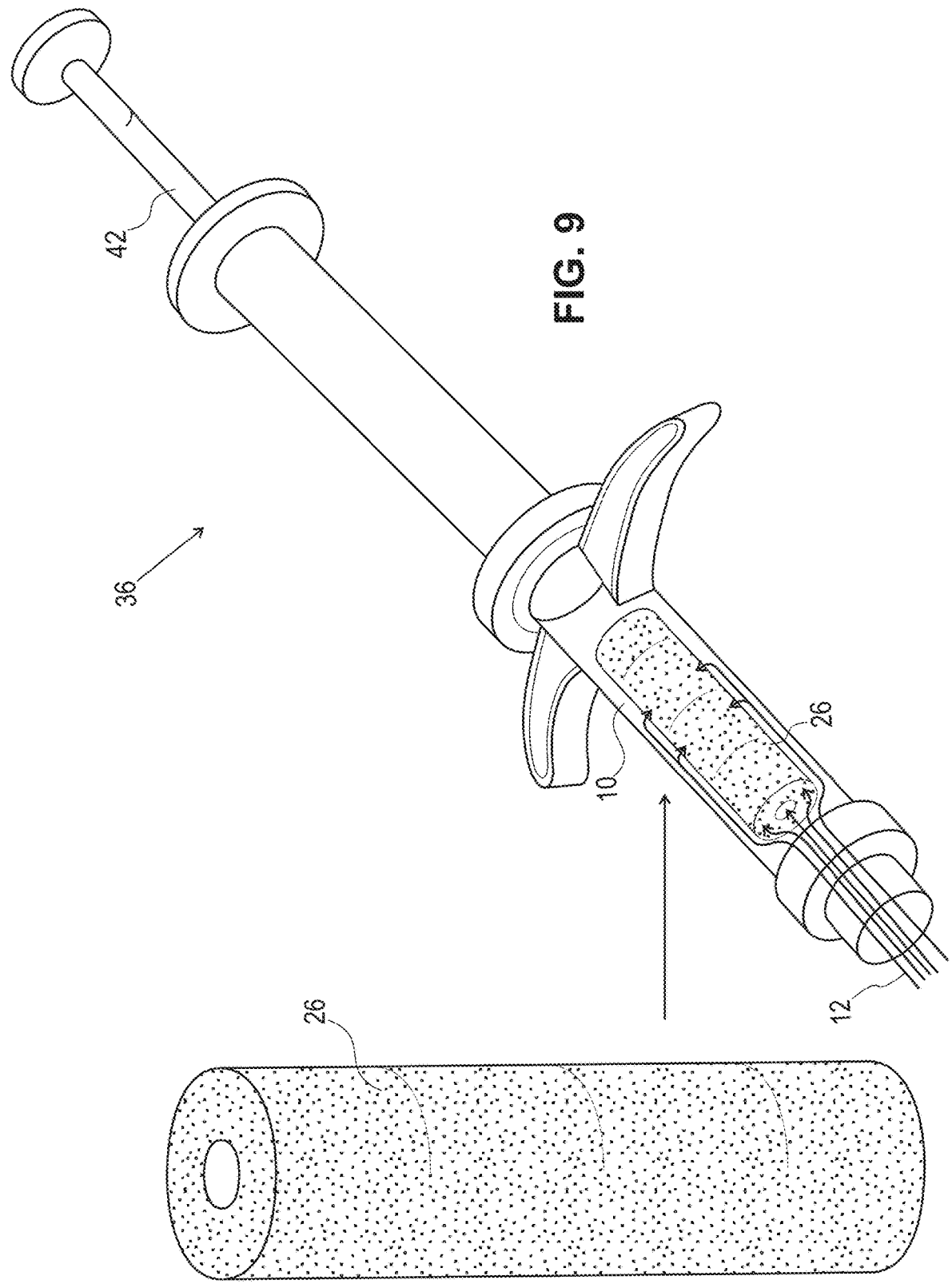
FIG. 9 is a perspective view of a lyophilized porous macroparticle shaped as a single hollow tube loaded into a chamber of a syringe. Fluid is added to the syringe and the fluid moves through the hollow tube and the fluid penetrates inwardly.

FIG. 9 shows the single hollow tube shaped macroparticle of FIG. 4 loaded into the chamber of the syringe. Fluid is added to the syringe and the fluid will move through the single hollow tube shape and the fluid will also penetrate inwardly into an interior channel of the tube.

Figure 10:
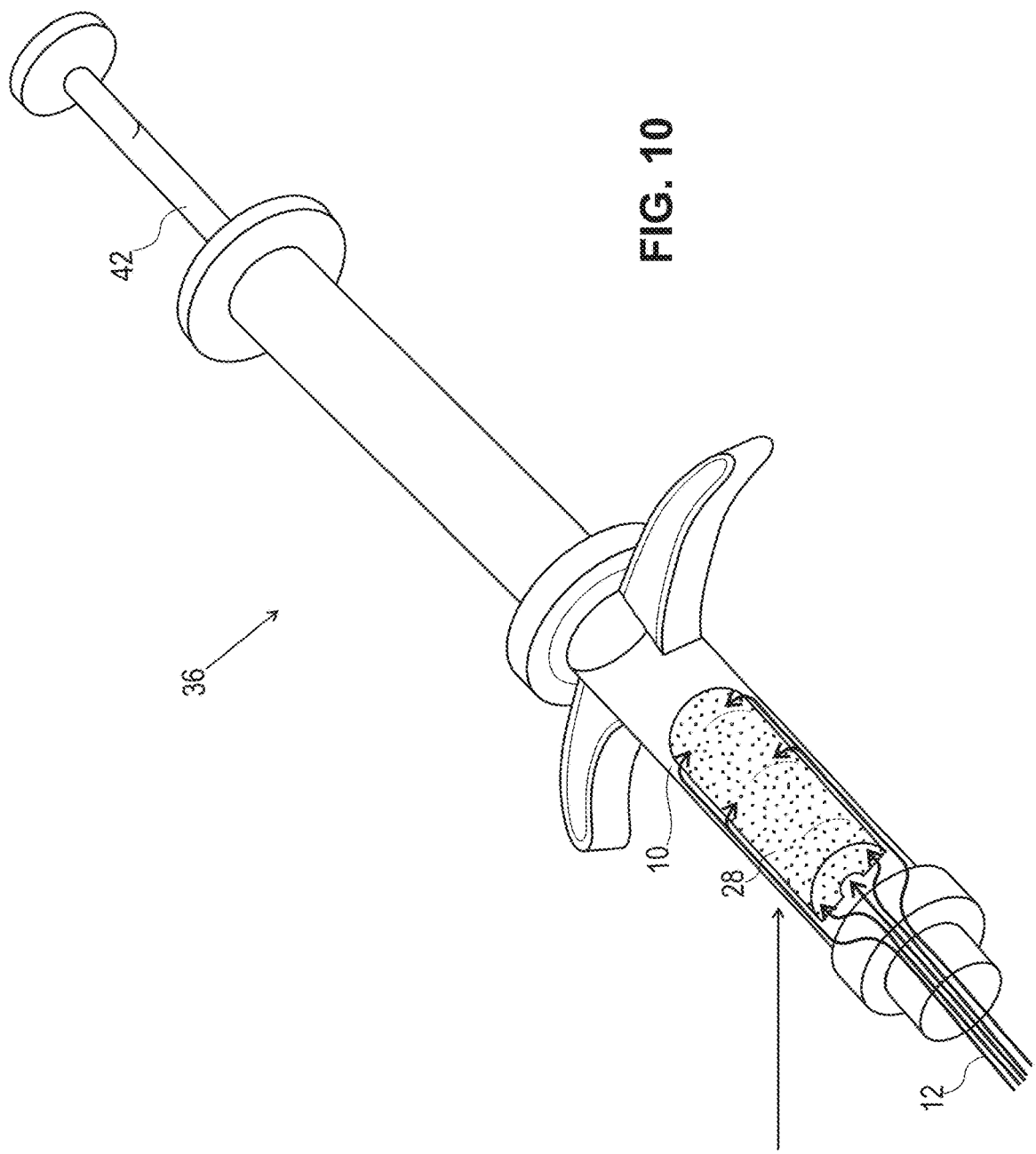
FIG. 10 is a perspective view of a lyophilized porous macroparticle shaped as a half or hemisphere of a single hollow tube loaded into a chamber of a syringe. Fluid is added to the syringe and the fluid penetrates inwardly.

FIG. 10 shows the half or hemisphere of a single hollow tube of FIG. 5 loaded into the chamber of the syringe. Fluid is added to the syringe and the fluid will penetrate inwardly into the tube.

FIG. 11 shows two halves or hemispheres of the hollow tube of FIG. 5 loaded into the chamber of the syringe. Fluid is added to the syringe and the fluid flows concentrically from both internal and external sides. The two halves of the hollow tube can be loaded into the chamber to increase surface area for hydration.

Figure 14:
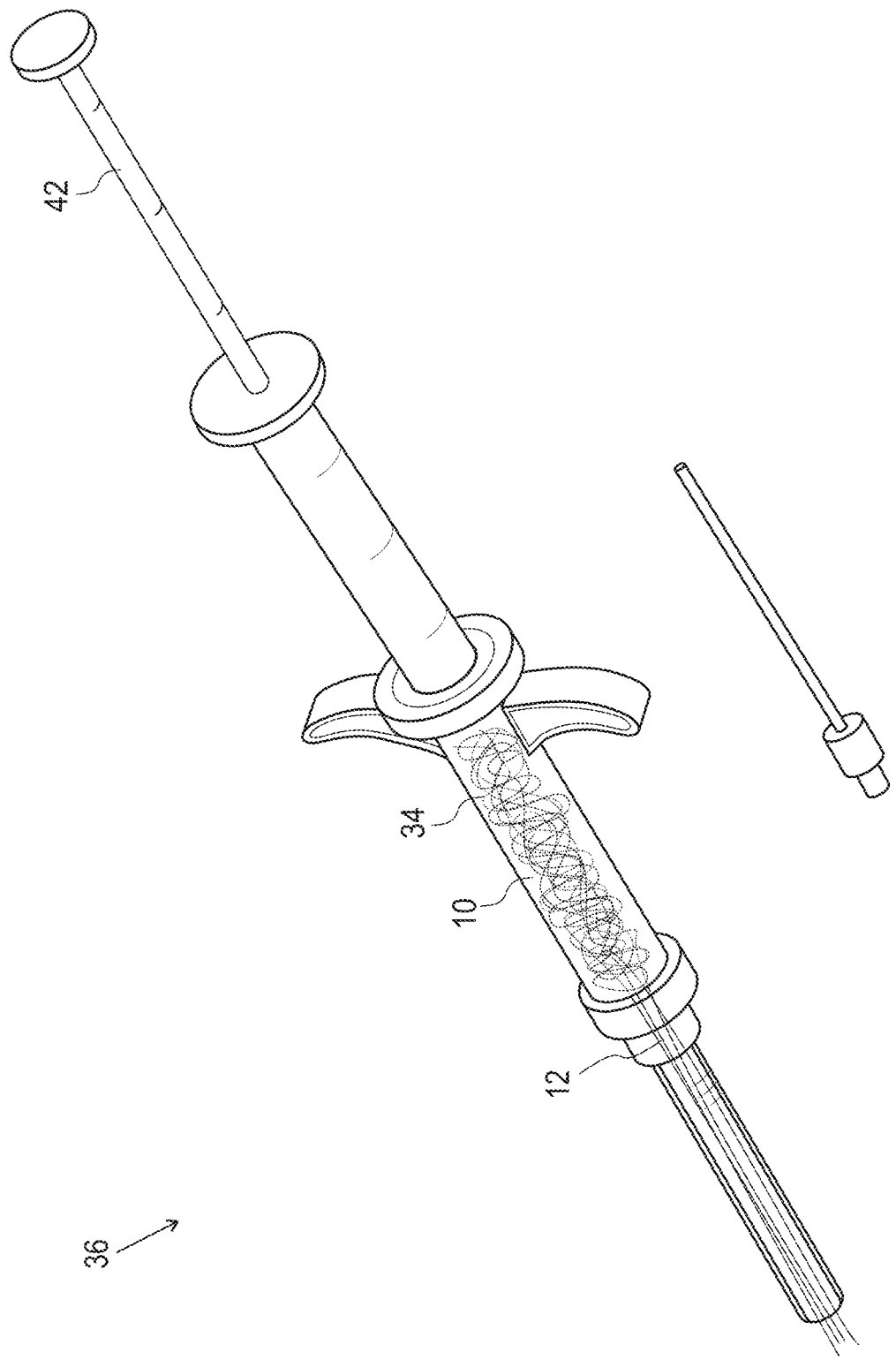
FIG. 14 is a perspective view of a plurality of lyophilized porous macroparticles shaped as electrospun fibers loaded into a chamber of a syringe. Fluid is added to the syringe and the fluid disperses throughout the electrospun fibers.
Figure 15B:
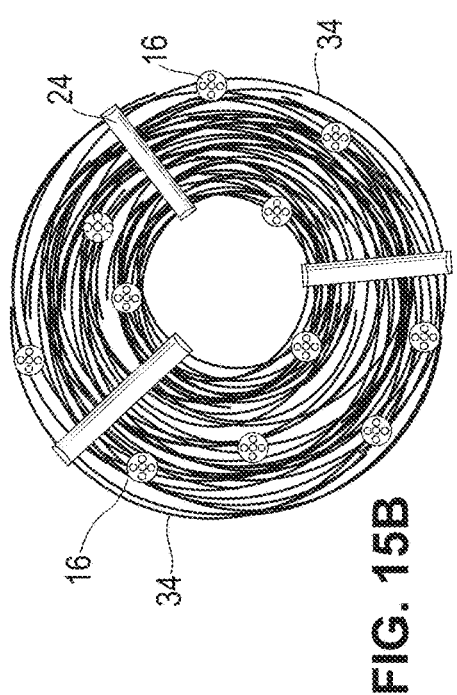
FIG. 15B is a perspective view of the electrospun fibers of FIG. 15 configured as into a ball.
Figure 15:
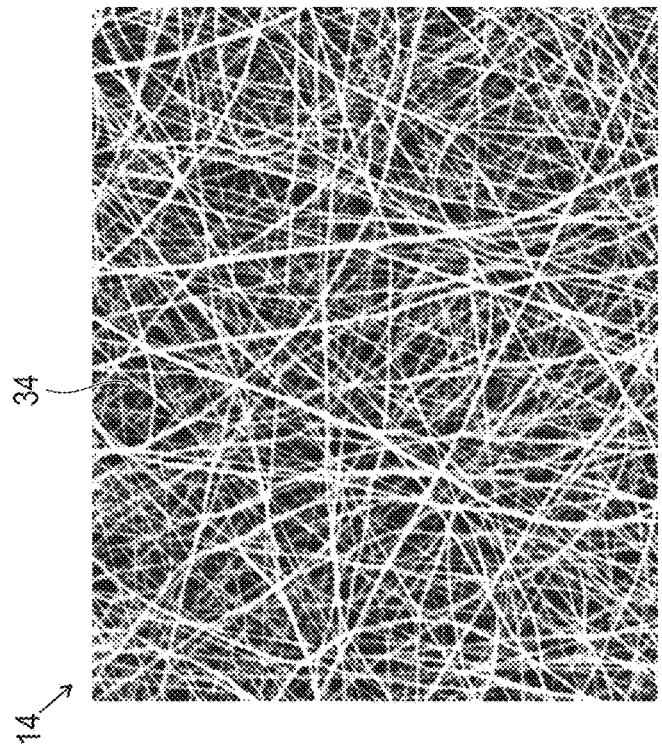
FIG. 15 is a contemplative SEM rendering of the electrospun fibers of FIG. 14. The electrospun fibers are made of a polymer embedded with the ceramic material comprising porous ceramic granules.

As shown in FIGS. 14-15B and described above, macroparticles can be shaped as electrospun fibers. The fibers can be made from the polymer, such as collagen and are embedded with the ceramic material in porous ceramic granule form, as shown in FIG. 15A. The electrospun fiber shape can provide maximum surface area for maximum hydration, ease of hydration and minimum hydration time.

The electrospun polymer fibers can have an average length from about 1 mm to about 50 mm or from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 to about 50 mm. The electrospun polymer fibers can have an average diameter from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9 to about 10 mm.

In some embodiments, the appearance of the final form of the composition comprising electrospun fibers can be in a "cotton ball" shape, as shown in FIG. 15B. The cotton ball shape can also include electrospun rods and/or ceramic material shaped as rods 24.

FIG. 14 shows electrospun fibers loaded into the chamber of the syringe. Fluid is added to the syringe and the fluid disperses throughout the electrospun fibers. The electrospun fibers uniformly hydrate creating a flowable composition.

The fluid used to hydrate the macroparticles can include bone marrow aspirate, saline, sterile water, blood for injection, phosphate buffered saline, dextrose, Ringer's lactated solution, or a combination thereof. The ratio of fluid to the plurality of lyophilized porous macroparticles can be from about 0.5:1 to about 3:1. In some embodiments, the ratio of fluid to the plurality of lyophilized porous macroparticles can be from about 0.5:1, 0.6:1, 0.7:1, 0.8:1, 0.9:1, 1:1, 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1 to about 3:1.

Figure 12:
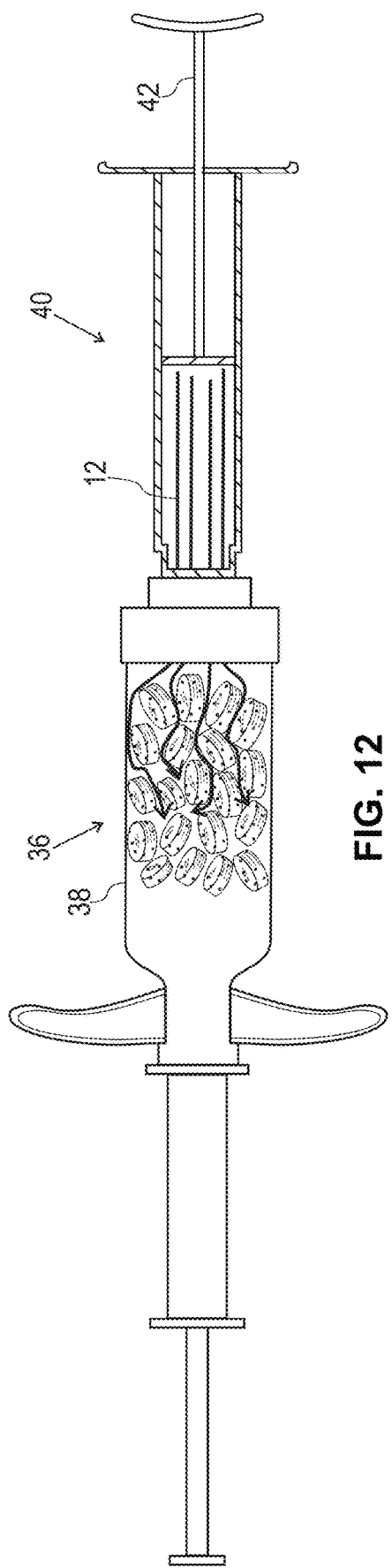
FIG. 12 is a side view of a hydration method where a plurality of lyophilized porous macroparticles shaped as cylinders are loaded into a chamber of a syringe. The syringe is then connected to a second syringe that is loaded with a fluid such as the patient's own blood, bone marrow aspirate (BMA) or water and the fluid is inserted into the syringe loaded with the macroparticles. The fluid can be pumped into the chamber loaded with the macroparticles or the fluid can be injected without the need for pumping. If the fluid is injected without pumping, the macroparticles are soaked for a period of time with the fluid.
Figure 13:
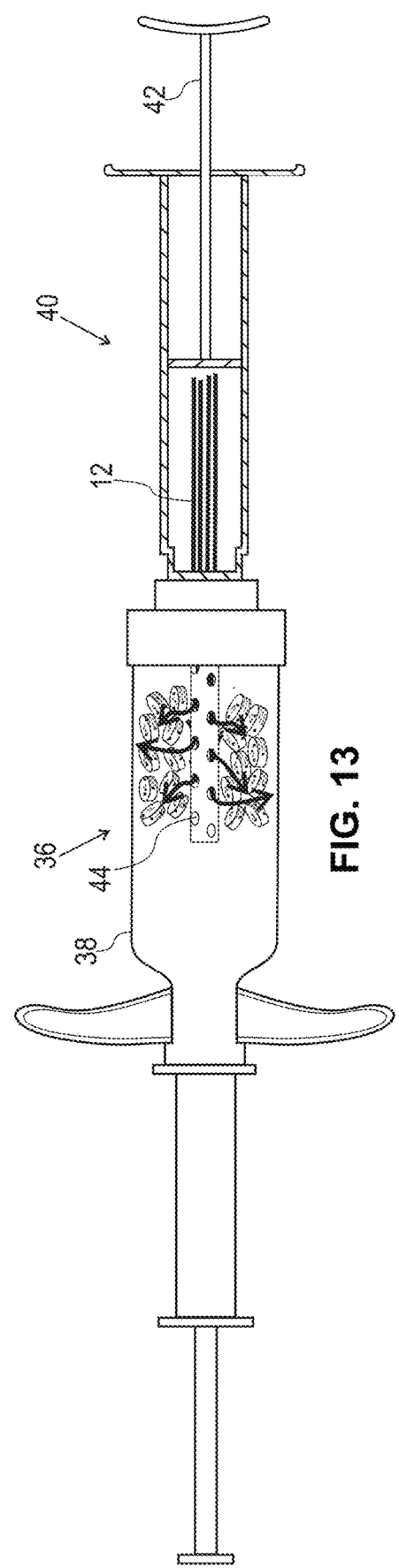
FIG. 13 is a side view of a hydration method similar to the method shown in FIG. 12.

In some embodiments, as shown in FIGS. 12 and 13 and described above, the composition can be hydrated in the syringe. In FIG. 12, the plurality of lyophilized porous macroparticles shaped as cylinders are loaded into the chamber of the syringe. The syringe is then connected to a second syringe 40 that is loaded with the fluid and includes a plunger 42 that dispenses the fluid from the second syringe. The fluid can be the patient's own blood, bone marrow aspirate (BMA) or water. The fluid is inserted into the first syringe loaded with the macroparticles. In some embodiments, the fluid can be pumped into the chamber of the first syringe by the plunger or the fluid can be injected without the need for pumping. If the fluid is injected without pumping, the macroparticles are soak for a period of time with the fluid. In FIG. 13, the syringe includes a fenestrated needle 44 to increase the speed of hydration of the macroparticles. A fenestrated needle can also minimize dry/unhydrated macroparticles to improve injectability.

Autograft bone can be added to the hydratable composition before or after hydration. The autograft bone can be cut into various shapes, including fibers, chips, granules, powder, shards, shavings or a combination thereof. The autograft bone can be cut into specific sizes. For example, the autograft bone can be from about 1 to about 10 mm. In some embodiments, the size of the autograft bone added to the composition can be from about 1, 2, 3, 4, 5, 6, 7, 8, 9 to about 10 mm. In some embodiments, the autograft bone is cut into bone chips having a size from about 1 to about 4 mm and is added to the hydratable composition after hydration.

A certain amount of autograft bone can be added to the hydratable composition, such as from about 0 to about 50 vol. % or from about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 to about 50 vol. % based on the total weight of the hydratable composition. In some embodiments, the composition can contain greater than 50 vol. % of autograft bone without the composition losing its cohesive properties.

In some embodiments, the hydratable composition has a flowable viscosity starting from about 50 Pascal-second (Pa-s), 100 Pa-s, 150 Pa-s, 200 Pa-s, 250 Pa-s, to about 300 Pa-s and reaches a higher viscosity from about 500 Pa-s, 750 Pa-s, 1000 Pa-s, 1500, 2000 Pa-s, 2500 Pa-s to about 3000 Pa-s. In some embodiments, the hydratable composition has a flowable viscosity starting from about 50 Pa-s to about 3000 Pa-s and reaches a higher viscosity from about 3000 Pa-s to about 300,000 Pa-s.

The hydratable composition can have a certain density when hydrated. For example, when the composition is hydrated, the density can be from about 1.2 to about 2.0 g/cc or from about 1.4 to about 1.6 g/cc. In some embodiments, the hydrated composition can have a density from about 1.2, 1.3, 1.4, 1.5, 1.6, 1.7, 1.8, 1.9 to about 2.0 g/cc.

The hydratable composition can have a modulus of elasticity from about 2 MPa to about 12 MPa, such as from about 2, 3, 4, 5, 6, 7, 8, 9, 10, 11 to about 12 MPa.

In some embodiments, if autograft bone is added to the composition after hydration, the modulus of elasticity can be increased with the addition of the autograft bone.

In some embodiments, the fluid used to hydrate the composition can include sterile water, saline, phosphate buffered saline (PBS), hyaluronic acid, cellulose ethers (such as carboxymethyl cellulose), water, collagen, gelatin, autoclaved bone powder, osteoconductive carriers, whole blood, blood fractions, concentrated bone marrow aspirate, and mixtures thereof. Non-limiting examples of blood fractions include serum, plasma, platelet-rich plasma, concentrated platelet-rich plasma, platelet-poor plasma, and concentrated platelet poor plasma.

A viscosity enhancing agent can be added to the composition including, but not limited to mannitol, trehalose, hydroxypropyl cellulose, hydroxypropyl methylcellulose, hydroxyethyl methylcellulose, carboxymethylcellulose and salts thereof, Carbopol, poly-(hydroxyethyl-methacrylate), poly-(methoxyethylmethacrylate), poly(methoxyethoxyethylmethacrylate), polymethyl-methacrylate (PMMA), methylmethacrylate (MMA), gelatin, polyvinyl alcohols, propylene glycol, mPEG, PEG 200, PEG 300, PEG 400, PEG 500, PEG 600, PEG 700, PEG 800, PEG 900, PEG 1000, PEG 1450, PEG 3350, PEG 4500, PEG 8000 or combinations thereof.

In some embodiments, additional materials may be added to the composition such as one or more of poly(alpha-hydroxy acids), polyglycolide (PG), polyethylene glycol (PEG) conjugates of poly(alpha-hydroxy acids), polyorthoesters (POE), polyaspirins, polyphosphagenes, gelatin, hydrolyzed gelatin, fractions of hydrolyzed gelatin, elastin, starch, pre-gelatinized starch, hyaluronic acid, chitosan, alginate, albumin, fibrin, vitamin E analogs, such as alpha tocopheryl acetate, d-alpha tocopheryl succinate, D,L-lactide, or L-lactide, caprolactone, dextrans, vinylpyrrolidone, polyvinyl alcohol (PVA), PVA-g-PLGA, PEGT-PBT copolymer (polyactive), methacrylates, PEO-PPO-PAA copolymers, PLGA-PEO-PLGA, PEG-PLG, PLA-PLGA, poloxamer 407, PEG-PLGA-PEG triblock copolymers, POE, SAIB (sucrose acetate isobutyrate), polydioxanone, methylmethacrylate (MMA), MMA and N-vinylpyyrolidone, polyamide, oxycellulose, copolymer of glycolic acid and trimethylene carbonate, polyesteramides, polyether ether ketone, polymethylmethacrylate, silicone, hyaluronic acid, or combinations thereof.

In some embodiments, the macroparticles can alternatively or in addition to comprise at least one biodegradable polymer comprising one or more of poly(lactide-co-glycolide) (PLGA), polylactide (PLA), polyglycolide (PGA), D-lactide, D,L-lactide, L-lactide, D,L-lactide-co-ε-caprolactone, L-lactide-co-ε-caprolactone, D,L-lactide-co-glycolide-co-ε-caprolactone, poly(D,L-lactide-co-caprolactone), poly(L-lactide-co-caprolactone), poly(D-lactide-co-caprolactone), poly(D,L-lactide), poly(D-lactide), poly(L-lactide), poly(esteramide), carboxymethylcellulose (CMC), alkylene oxide copolymer (AOC) or a combination thereof.

In some embodiments, the macroparticles can alternatively or in addition to comprise at least one ceramic material, including, but not limited to synthetic ceramics selected from one or more materials comprising calcium phosphate ceramics or silicon ceramics. Biological glasses such as calcium-silicate-based bioglass, silicon calcium phosphate, tricalcium phosphate (TCP), biphasic calcium phosphate, calcium sulfate, hydroxyapatite, coralline hydroxyapatite, silicon carbide, silicon nitride ($Si_3N_4$), and biocompatible ceramics may be used. In some embodiments, the ceramic material is tri-calcium phosphate or biphasic calcium phosphate and silicon ceramics. In some embodiments, the ceramic material is tricalcium phosphate.

In some embodiments, the ceramic material is a combination of a calcium phosphate ceramic and a silicon ceramic. In some embodiments, the calcium phosphate ceramic is resorbable biphasic calcium phosphate (BCP) or resorbable tri-calcium phosphate (TCP).

The ceramic material of the disclosure may also be oxide ceramics such as alumina ($Al_2O_3$) or zirconia ($ZrO_2$) or composite combinations of oxides and non-oxides such as silicon nitride.

Lyophilization

As described herein, the composition and its components, such as the macroparticles can be lyophilized. The lyophilization process typically includes sublimation of water from a frozen formulation under controlled conditions. Lyophilization can be carried out using standard equipment as used for lyophilization or vacuum drying. The cycle may be varied depending upon the equipment and facilities used for the fill and finish.

Initially, in some embodiments, the combined materials that create the macroparticles (e.g., the ceramic material combined with the polymer) is placed in a lyophilization chamber under a range of temperatures and then subjected to temperatures well below the freezing point of the materials, generally for several hours. After freezing is complete, the lyophilization chamber and the condenser are evacuated through vacuum pumps, the condenser surface having been previously chilled by circulating refrigerant. The condenser will have been chilled below the freezing point of the materials. Additionally, evacuation of the chamber should continue until a pressure of about 50 mTorr to about 600 mTorr, preferably about 50 to about 150 mTorr is obtained.

The lyophilized material is then warmed under vacuum in the chamber and condenser. This usually will be carried out by warming the shelves within the lyophilizer on which the lyophilized composition rests during the lyophilization process at a pressure ranging from about 50 mTorr to about 600 mTorr. The warming process will optimally take place very gradually, over the course of several hours. Complete drying can be accomplished by stabilization of vacuum, condenser temperature and lyophilized composition shelf temperature. After the initial drying, the temperature of the lyophilized material can be increased and maintained for several hours. Once the drying cycle is completed, the pressure in the chamber can be slowly released to atmospheric pressure (or slightly below) with sterile, dry-nitrogen gas (or equivalent gas).

In some embodiments, after lyophilization, the material that forms the macroparticles is from about 95 to about 99.5% free of moisture. The material can be from about 95, 95.5, 96, 96.5, 97, 97.5, 98, 98.5, 99, to about 99.5% free of moisture. In some embodiments, the material has about 0.5% to about 5% moisture content remaining after lyophilization. In various embodiments, the material has from about 0.5, 1, 1.5, 2, 2.5, 3, 3.5, 4, 4.5 to about 5% moisture content remaining after lyophilization. The lyophilized material is stable and can be stored at a wide range of temperatures.

Methods of Making

A method of making a uniformly hydrated composition is provided. The method comprises providing a plurality of lyophilized porous macroparticles in a chamber, the plurality of lyophilized porous macroparticles each having an average diameter from about 0.1 mm to about 10 mm and comprising ceramic material and polymer; and mixing each of the plurality of lyophilized porous macroparticles with a fluid in the chamber to uniformly hydrate each of the plurality of lyophilized porous macroparticles to form a uniformly hydrated composition. It is to be understood that the composition described is hydratable composition 10 described above.

The ratio of fluid to the plurality of lyophilized porous macroparticles can be from about 1:1 to about 3:1. In some embodiments, the ceramic is in an amount from about 50 to about 98 wt. % and the polymer is in an amount from about 2 to about 50 wt. % based on a total weight of each of the lyophilized porous macroparticles. The plurality of lyophilized porous macroparticles in the chamber can have a packing density to maximize hydration of the plurality of lyophilized porous macroparticles. In some embodiments, the plurality of lyophilized porous macroparticles has shapes comprising cylinders, cubes, rods, tubes, hollow tubes, rectangles, discs, half hemispherical hollow tubes, electrospun fibers, or a combination thereof.

In various embodiments, gamma radiation is used to sterilize the composition, which involves utilizing ionizing energy from gamma rays that penetrates deeply into the composition. Gamma rays are highly effective in killing microorganisms, they leave no residues nor have sufficient energy to impart radioactivity to the composition. Gamma rays can be employed when the composition is packaged and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize the composition. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly charged streams of electrons generated by the acceleration and conversion of electricity.

Other methods may also be used to sterilize the composition, including, but not limited to, gas sterilization, such as, for example, with ethylene oxide or steam sterilization.

In some embodiments, the composition can be used as a bone graft in any suitable application. For example, the composition can be administered as a bone graft which can be utilized in a wide variety of orthopedic, periodontal, neurosurgical, oral and maxillofacial surgical procedures such as the repair of simple and/or compound fractures and/or non-unions; external and/or internal fixations; joint reconstructions such as arthrodesis; general arthroplasty; cup arthroplasty of the hip; femoral and humeral head replacement; femoral head surface replacement and/or total joint replacement; repairs of the vertebral column including spinal fusion and internal fixation; tumor surgery, e.g., deficit filling; discectomy; laminectomy; excision of spinal cord tumors; anterior cervical and thoracic operations; repairs of spinal injuries; scoliosis, lordosis and kyphosis treatments; intermaxillary fixation of fractures; mentoplasty; temporomandibular joint replacement; alveolar ridge augmentation and reconstruction; inlay implantable matrices; implant placement and revision; sinus lifts; cosmetic procedures; etc. Specific bones which can be repaired herein include the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal and/or metatarsal bones.

In some embodiments, a method of making macroparticles in the shape of electrospun fibers is provided. The method comprises adding a polymer carrier into a solution such as a volatile solvent and then dissolving or heating the polymer. The ceramic material in granule form is then added to the solution. The solution is then placed into an electrospinning machine. The end result creates electrospun polymer fibers embedded with ceramic granules. It is to be understood that the electrospun fibers can be manufactured by single injection or multi injection systems. In some embodiments, the method employs coaxial electrospinning, emulsion electrospinning or melt electrospinning techniques.

In some embodiments, electrospinning parameters include, but are not limited to, molecular weight of the parameter, molecular-weight distribution and architecture (e.g., branched or linear) of the polymer, solution properties (e.g., viscosity, conductivity and surface tension), electric potential, flow rate and concentration, distance between the capillary and collection screen, ambient parameters (e.g., temperature, humidity and air velocity in the chamber), motion and size of target screen (collector), and needle gauge.

In some embodiments, the term "solution" is used to describe the liquid in the reservoirs of the electrospinning method. The term is defined broadly to include any liquids that contain materials to be electrospun. It is to be understood that any solutions capable of forming a material during electrospinning are included within the scope of the present application. In this application, the term "solution" also refers to suspensions or emulsions containing the material or anything to be electrodeposited. "Solutions" can be in organic or biologically compatible forms. This broad definition is appropriate in view of the large number of solvents or other liquids and carrier molecules, such as poly(ethylene oxide) (PEO), that can be used in the many variations of electrospinning. In this application, the term "solution" also refers to melts, hydrated gels and suspensions containing the materials, substances or anything to be electrodeposited.

In some embodiments, the solution can be water, 2,2,2-trifluoroethanol, 1,1,1,3,3,3-hexafluoro-2-propanol (also known as hexafluoroisopropanol or HFIP), urea, monochloroacetic acid, HFIP, isopropanol, HFIP, lower order alcohols such as halogenated alcohols, acetamide, N-methylformamide, N,N-dimethylformamide (DMF), dimethylsulfoxide (DMSO), dimethylacetamide, N-methyl pyrrolidone (NMP), acetic acid, trifluoroacetic acid, ethyl acetate, acetonitrile, trifluoroacetic anhydride, 1,1,1-trifluoroacetone, maleic acid, and/or hexafluoroacetone.

One or more electroprocessing techniques can be employed as an alternative to electrospinning, such as, for example, electrospray, electroaerosol, electrosputter, or any combination thereof.

Kits

In various embodiments, a kit is provided comprising the hydratable composition and/or components of the hydratable composition such as the macroparticles and the fluid separate from the composition. The kit may include additional parts along with the composition combined together to be used to administer the composition (e.g., wipes, needles, syringes, mixing syringe or another mixing device, etc.). The kit may include the macroparticles or the macroparticles already added to composition in a first compartment. The second compartment may include any other instruments needed for the delivery. A third compartment may include the fluid for hydrating the composition. A fourth compartment may include gloves, drapes, wound dressings and other procedural supplies for maintaining sterility of the implanting process, as well as an instruction booklet, which may include a chart that shows how to administer the composition. A fifth compartment may include additional needles and/or sutures. Each tool may be separately packaged in a plastic pouch that is sterilized. A sixth compartment may include an agent for radiographic imaging. A cover of the kit may include illustrations of the implanting procedure and a clear plastic cover may be placed over the compartments to maintain sterility.

In some embodiments, the composition separate or in a kit can have a shelf life from 3 to about 5 years.

These and other aspects of the present application will be further appreciated upon consideration of the following Example, which is intended to illustrate a certain particular embodiment of the application but is not intended to limit its scope, as defined by the claims.

EXAMPLES

Example 1

Porous Ceramic Granules

Porous ceramic granules are contemplated that are made from the method found and described in U.S. application Ser. No. 16/523,259, filed on Jul. 26, 2019, assigned to Warsaw Orthopedic, Inc., which is incorporated herein by reference. The porous ceramic granules have an average diameter from about 50 μm to 800 μm, comprise a biphasic calcium phosphate comprising hydroxyapatite in an amount of about 8 to about 22 wt. % and beta-tricalcium phosphate in an amount of about 78 to about 92 wt. %, have a microporosity and the diameter of each of the micropores is from about 0.1 to about 10 microns, comprise an outer surface comprising a plurality of concave shapes each having a diameter of from about 400 to about 600 microns and each of the porous ceramic granules have a BET surface area from about 0.2 to about 10 $m^2/g$.

Example 2

Implantable Composition

An implantable composition is contemplated that can be in the form of a moldable putty or a non-settable flowable cohesive cement or gel. The implantable composition can be dehydrated and then hydrated into a moldable putty. The moldable putty can then be further hydrated into a non-settable flowable cohesive cement or gel.

It is contemplated that the implantable composition comprises porous ceramic granules comprising hydroxyapatite in an amount of about 8 to about 22 wt. % and beta-tricalcium phosphate in an amount of about 78 to about 92 wt. % based on a total weight of a ceramic granule; and a collagen carrier. The porous ceramic granules have an average diameter from about 50 μm to 800 μm. The composition comprises from about 50 to about 98 wt. % porous ceramic granules and from about 2 to about 50 wt. % collagen carrier based on a total weight of the composition. The collagen carrier is porcine or bovine collagen and the implantable composition has a modulus of elasticity from about 2 MPa to about 12 MPa. The implantable composition can be hydrated with bone marrow aspirate.

Example 3

Implantable Composition

An implantable composition is contemplated that can be in the form of a moldable putty or a non-settable flowable cohesive cement or gel. The implantable composition can be dehydrated and then hydrated into a moldable putty and/or a non-settable flowable cohesive cement or gel.

The implantable composition comprises porous ceramic granules comprising hydroxyapatite in an amount of about 15 wt. % and beta-tricalcium phosphate in an amount of about 85 wt. % based on a total weight of a ceramic granule and a collagen carrier. The calcium to phosphate ratio is 1.525. The porous ceramic granules have an average diameter from about 200 μm to 500 μm. The composition comprises from about 77 to about 93 wt. % porous ceramic granules and from about 7 to about 23 wt. % collagen carrier based on a total weight of the composition. The collagen carrier is bovine type I collagen and the plurality of concave shapes on the outer surface of the granules each have a diameter from about 400 to about 600 microns. The porous ceramic granules contain microporosity and the volume of the microporosity is from about 0.01 to about 10 microns. Each of the porous ceramic granules have a BET surface area from about 0.2 to about 0.6 $m^2/g$. The implantable composition can be hydrated with bone marrow aspirate.

Example 4

Flowable and Moldable Composition

Background: The handling characteristics (e.g. texture, compressive resistance, modulus of elasticity, and flowability) of the composition are important for implantation and use. Qualitative handling evaluation of the composition was performed to confirm cohesive and adhesive properties critical to putty moldability, modularity, combination with autograft, and versatility in known use conditions. Quantitative testing to characterize the handling properties was also performed and the results of this testing are briefly summarized below.

Texture Value

The texture value in arbitrary units is the positive area under the curve of an unconstrained load versus displacement curve under compression. Testing was performed on 1.5 cc of material hydrated with water at various hydration ratios (0.5-1.5 vol./vol.) and formed into a 10.25 mm diameter cylinder with 18 mm height. The test articles were compressed with a 5 mm diameter piston at a crosshead speed of 1.0 mm/s for 12 s.

Texture values of ≥200 were measured for test articles measured under the above conditions. Results showed that the texture value increased as the hydration level decreased. The texture value increased as the ceramic content and the ceramic granule size was increased. An optimal texture value for the composition in the moldable putty form (hydrated at 1:1 vol./vol.) was identified to be ≥1000. A lower texture value (e.g., 200-1000) was identified to be optimal for the flowable/injectable form (hydrated at >1:1 vol./vol.). The composition was determined to have these texture values after gamma irradiation at 25-40 kGy.

Young's Modulus of Elasticity

The modulus of elasticity of the composition was calculated from an unconstrained stress curve versus a strain curve when the composition was hydrated with water at various hydration ratios (0.5-1.5 vol./vol.), formed into a 10.25 mm diameter cylinder with 18 mm height, and compressed at a crosshead speed of 1.0 mm/s for 12 s.

The modulus of elasticity was calculated to be ≥2 MPa for test articles measured under the above conditions. The modulus of elasticity increased as the hydration level was decreased. The modulus of elasticity was increased as the ceramic content and ceramic granule size was increased. Optimal modulus of elasticity for the moldable putty and the flowable cement forms of the composition were identified after gamma irradiation at 25-40 kGy to be: ≥2 MPa, ≥6 MPa and ≥10 MPa.

Compressive Resistance-Peak Load

The peak load of the composition was measured from an unconstrained load versus displacement curve when the composition was hydrated with water at various hydration ratios (0.5-1.5 vol./vol.), formed into a 10.25 mm diameter cylinder with 18 mm height, and compressed at a crosshead speed of 1.0 mm/s for 12 s.

The peak load was measured to be 30≥gf≥500 for test articles measured under the above conditions. The peak load increased as the hydration level was decreased. The peak load was increased as the ceramic content and ceramic granule size was increased. Optimal peak loads for the moldable putty and flowable cement forms of the composition were identified after gamma irradiation at 25-40 kGy to be between: 30≥gf≥500, 50≥gf≥400 and 100≥gf≥400.

Example 5

Uniformly Hydratable Composition

Figure 16:
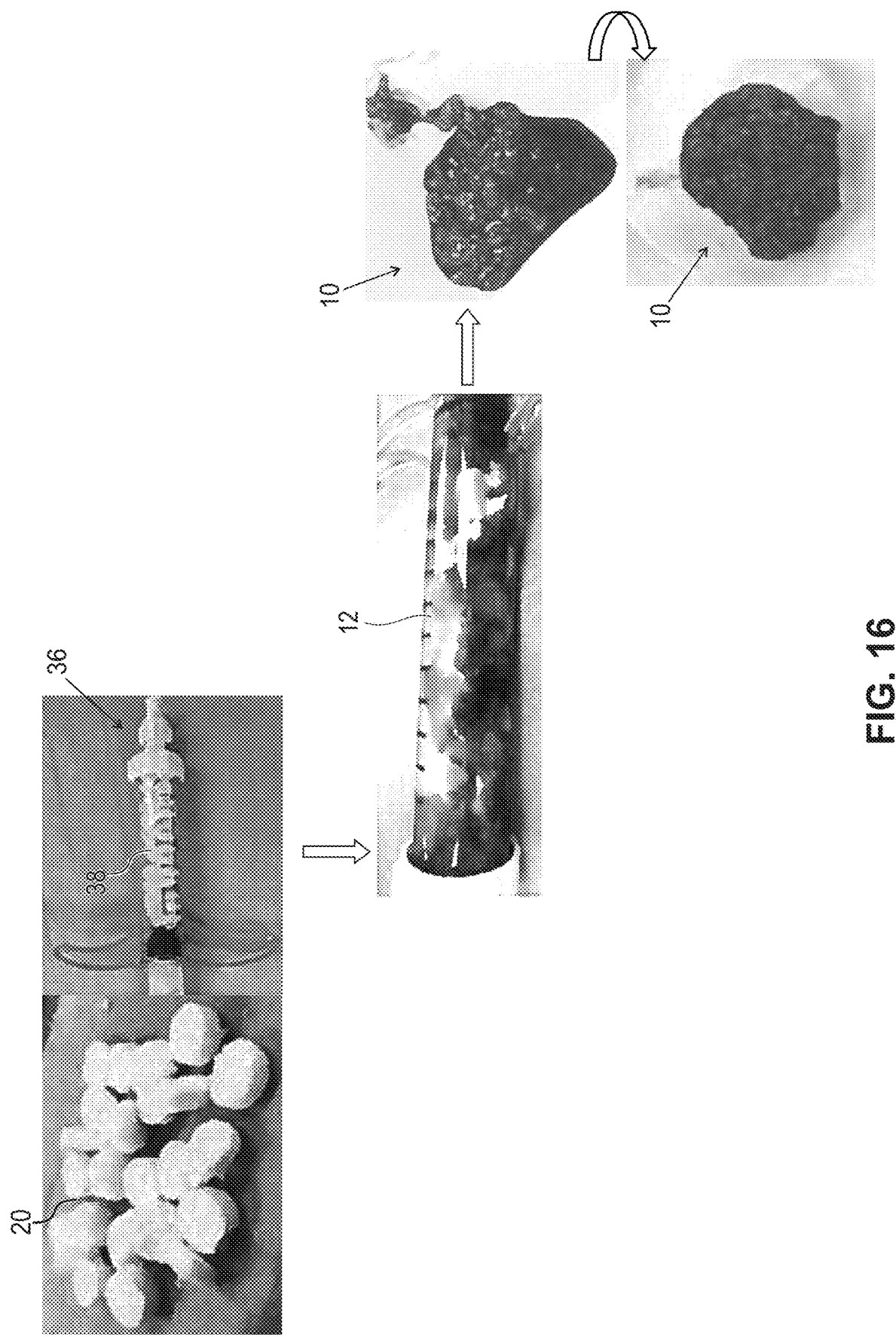
FIG. 16 is a perspective view of the steps in an experiment where a plurality of lyophilized porous macroparticles shaped as cylinders are loaded into a chamber of a syringe. The macroparticles are hydrated with blood resulting in a uniformly hydrated graft composition.

As shown in FIG. 16, uniform hydration of a composition comprising macroparticles comprising ceramic material and a polymer disposed in a closed container, such as a chamber of a syringe is disclosed. Before the macroparticles were formed into shapes, a sheet of ceramic material combined with a polymer was lyophilized then chopped with a biopsy punch into a plurality of porous macroparticles. The macroparticles were shaped as cylinders having an average diameter of about 8 mm and were loaded into a chamber of a syringe. The syringe used contained a fenestrated needle. The macroparticles were hydrated with blood inside of the syringe which resulted in a uniformly hydrated graft composition. The resulting composition was subsequently combined with simulated autograft bone. The autograft bone was in the form of 1 to 4 mm bone chips.

Figure 18:
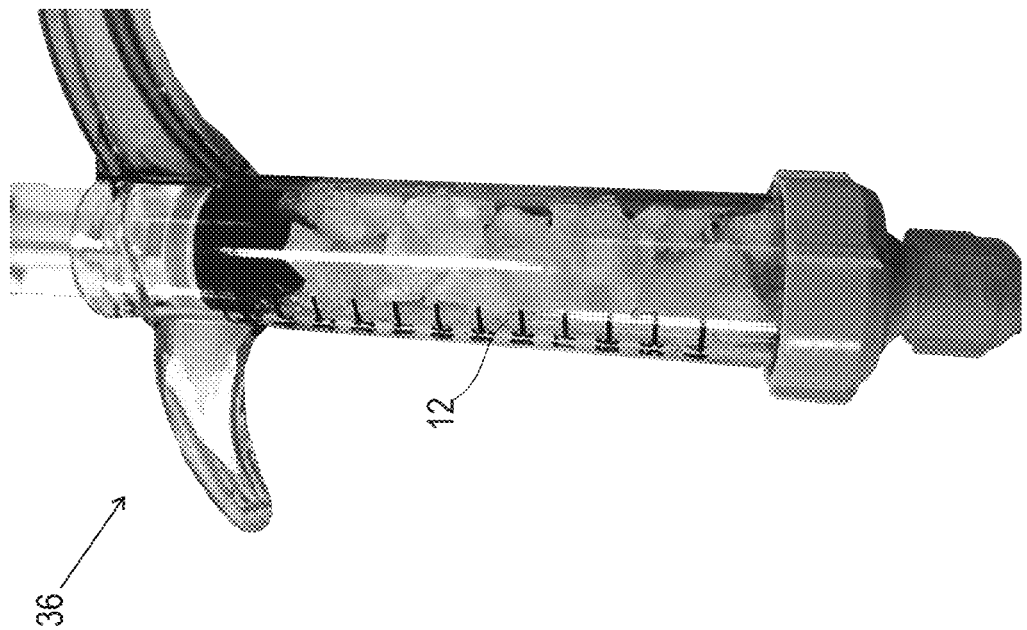
FIG. 18 is a perspective view of a plurality of lyophilized porous macroparticles loaded into a chamber of a syringe. Fluid is added to the syringe and the fluid moves around the plurality of lyophilized porous macroparticles uniformly.
Figure 17:
FIG. 17 is a perspective view of a plurality of lyophilized porous macroparticles loaded into a chamber of a syringe.
Figure 20:
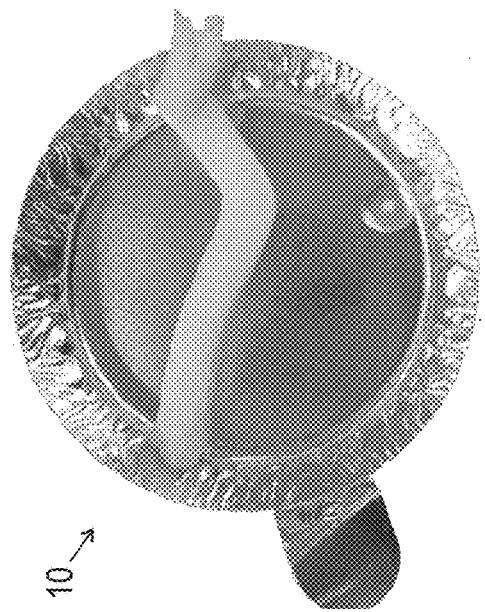
FIG. 20 illustrates lyophilized porous macroparticles hydrated with water and dispensed from the syringe in a ribbon like form.
Figure 22:
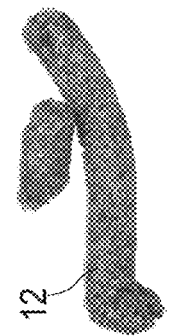
FIG. 22 illustrates lyophilized porous macroparticles hydrated with blood or bone marrow aspirate (BMA) and dispensed from the syringe in a ribbon like form.
Figure 19:
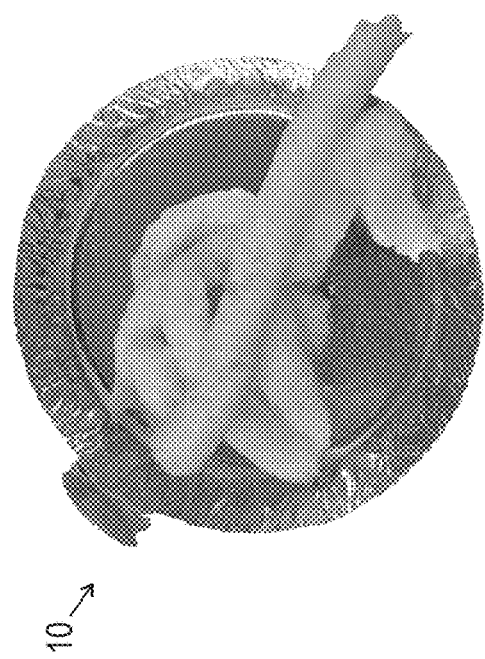
FIG. 19 illustrates lyophilized porous macroparticles hydrated with water and dispensed from the syringe in a ribbon like form.
Figure 21:
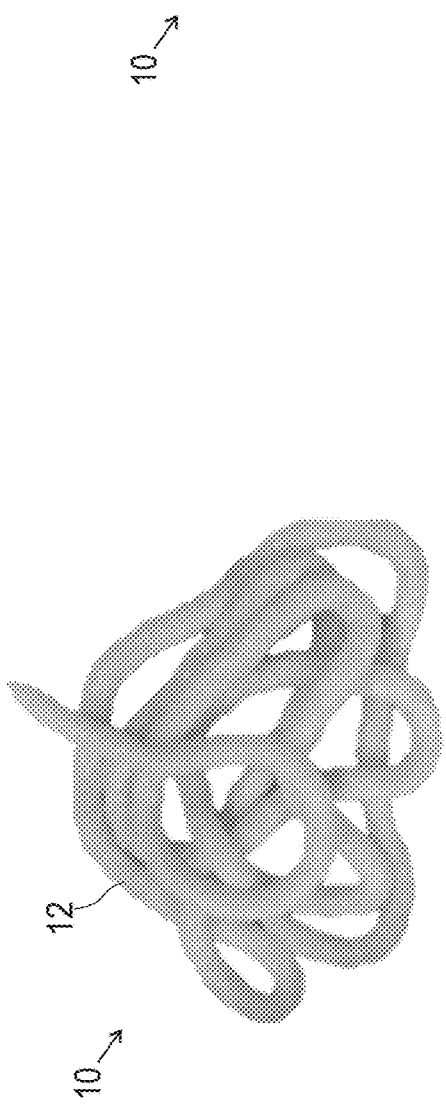
FIG. 21 illustrates lyophilized porous macroparticles hydrated with water and dispensed from the syringe in a ribbon like form.
Figure 25:
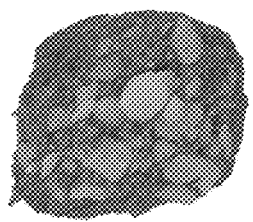
FIG. 25 illustrates a lyophilized porous macroparticle shaped as a cube that contains blood or BMA.
Figure 24:
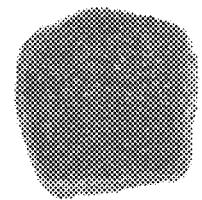
FIG. 24 illustrates a lyophilized porous macroparticle shaped as a cube that contains blood or BMA.
Figure 23:
FIG. 23 illustrates a lyophilized porous macroparticle shaped as a cube.

In FIGS. 23-25, the macroparticles are shown shaped as cubes 22, which can be hydrated with fluid (e.g., water, blood, BMA, etc.). The desired shape of the macroparticles can be obtained by filling macroparticles into a mold and then lyophilizing them and removing them from the mold in the desired shape (e.g., pellet, cylinder, cube, etc.). The macroparticles can be uniformly hydrated with fluid by placing them into a mixing device as shown in FIGS. 17 and 18. The macroparticles are loaded in chamber 38 of FIG. 17 and hydrated with fluid 12 shown as water in syringe 36 of FIG. 18 until the desired consistency is reached and the composition is uniformly hydrated. The hydrated macroparticles can be dispensed in ribbon like form after hydrating them with water as shown in FIGS. 19, 20 and 21 or hydrating them with blood or BMA as shown in FIG. 22. The dispensed macroparticles in ribbon like form can be molded into the tubular shape by hand as shown in FIG. 26. The syringe as illustrated in FIG. 18 did not have a fenestrated needle. It will be understood when hydrating the macroparticles (e.g., pellets) with fluid, an adapter with a fenestrated needle can be used or a standard adapter with no needle can be used.

Example 6

Hydration of Compositions with Different Macroform Parameters

Objective

The objective of this experiment was to further evaluate hydration of the composition within the barrel of a Nordson Syringe with a variation of macroform shape, size, density, packing, and hydration parameters for a pre-loaded syringe product.

Methods

Before the macroforms were formed into shapes, a sheet of ceramic material combined with a polymer was sterilized with gamma radiation at 25-40 kGy and lyophilized. The sheet was then chopped into cylinder macroforms with 4 mm and 6 mm biopsy punches. The macroforms were hydrated with heated (37° C.) bovine blood. Specifically, the 4 mm macroforms and the 6 mm macroforms were each loaded separately into a Nordson Syringe barrel. Syringe plungers were then compressed to determine macroform(s) packing density. Subsequently, blood was added to the syringes through a fenestrated needle attachment. The syringes were left stationary for 10 minutes on the benchtop to allow for sufficient soak time. The compositions in putty form were then injected down the cannulas and into weigh boats. The injected putty was combined at a 1:1 v/v hydration ratio to simulate combination with autograft (1-4 mm bovine bone chips).

Results

The lyophilized sheet of ceramic material combined with a polymer was easily prepared into macroforms and minimal compression or loss of putty thickness was observed. As expected, the smaller macroforms of 4 mm and 6 mm exhibited smoother hydration compared to previously evaluated 8 mm macroforms and took up less space within the syringe. A 10-minute benchtop soak time is sufficient time for hydration at the attempted volumes.

Putty injection with the syringe and cannula was performed with ease and no clogging. Macroform cylinder size, density, surface area (SA), volume, surface area-to-volume ratio (SAVR) and packing density were determined/calculated for each macroform size, as shown in Table 1.

As shown in Table 1 below, the following macroform parameters can be used. The macroform diameter range from 4 to 6 mm obtained a smooth and cohesive injection but a range from about 0.2 to about 10 mm can also be used. Macroform density from 0.1 to 0.6 g/cc obtained a smooth and cohesive injection but a range from about 0.1 to about 0.75 g/cc can also be used. The macroforms had a SAVR from 10 to 30. There should be a packing density within the syringe that allows for equal volumes of macroforms and open space such that fluid can fill the open space volume (1:1 ratio). Packing density within the syringe can be in a range from 0.2 to 1.0 g/cc compressed. When fluid for hydration was added in a 1:1 g/g and in a 2:1 g/g ratio, all final hydrated graft volumes were similar (1.75 to 2 cc) regardless of macroform size.

TABLE 1

Macroform parameters

| Macroform Diameter (mm) | Macroform SAVR (cm3/cm3) | Macroform Density (g/cc) | Mass of Macroforms Loaded (g) | Packing Density in syringe compressed (g/cc) | Fluid Added for hydration (cc water) | Final hydrated graft volume (cc) |
|---|---|---|---|---|---|---|
| 4 | 18 | 0.54 | 1.36 | 0.27 | 1.5 | 1.75 |
| 4 | 18 | 0.57 | 1.50 | 0.3 | 3.5 | 2 |
| 6 | 13.3 | 0.35 | 1.47 | 0.24 | 1.5 | 1.75 |
| 6 | 13.3 | 0.31 | 1.52 | 0.25 | 3 | 2 |

Although the invention has been described with reference to preferred embodiments, persons skilled in the art will recognize that changes may be made in form and detail without departing from the spirit and scope of the invention.

What is claimed is:

1. A method of making a uniformly hydrated composition, the method comprising providing a plurality of lyophilized porous macroparticles in a chamber, the plurality of lyophilized porous macroparticles each having an average diameter about 0.1 mm to about 10 mm and comprising ceramic material and polymer; and mixing each of the plurality of lyophilized porous macroparticles with a fluid in the chamber to uniformly hydrate each of the plurality of lyophilized porous macroparticles to form a uniformly hydrated composition, wherein the ceramic material comprises hydroxyapatite and beta-tricalcium phosphate having a calcium to phosphate ratio of between 1.0 to about 2.0, and the ceramic material is in the form of macroparticles having an average diameter from about 4 mm to about 6 mm and a density of 0.1 to 0.6 g/cc.

2. The method of claim 1, wherein (i) the ratio of fluid to the plurality of lyophilized porous macroparticles is from about 1:1 to about 3:1; or (ii) the ceramic is in an amount from about 50 to about 98 wt. % and the polymer is in an amount from about 2 to about 50 wt. % based on a total weight of each of the lyophilized porous macroparticles.

3. The method of claim 1, wherein the plurality of lyophilized porous macroparticles in the chamber has a packing density to maximize hydration of the plurality of lyophilized porous macroparticles.

4. The method of claim 1, wherein the plurality of lyophilized porous macroparticles has shapes comprising cylinders, cubes, rods, tubes, hollow tubes, rectangles, discs, half hemispherical hollow tubes, electrospun fibers, or a combination thereof.

5. A uniformly hydrated composition made by the method of claim 1, the uniformly hydrated composition comprising a plurality of lyophilized porous macroparticles comprising ceramic material in an amount from about 50 to about 98 wt. %, the ceramic material comprising hydroxyapatite and beta-tricalcium phosphate having a calcium to phosphate ratio of between 1.0 to about 2.0, the ceramic material is in the form of macroparticles having an average diameter from about 4 mm to about 6 mm and a density of 0.1 to 0.6 g/cc, and a polymer in an amount from about 2 to about 50 wt. % based on a total weight of each of the lyophilized porous macroparticles, each of the lyophilized porous macroparticles having an average diameter from about 0.1 mm to about 10 mm.

6. The composition of claim 5, wherein the polymer is (i) porcine or bovine collagen; (ii) bovine type I collagen; or (iii) tendon or dermis derived collagen.

7. The composition of claim 5, wherein the plurality of lyophilized porous macroparticles has shapes comprising cylinders, cubes, rods, tubes, hollow tubes, rectangles, discs, half hemispherical hollow tubes, electrospun fibers, or a combination thereof.

8. The composition of claim 5, wherein the plurality of lyophilized porous macroparticles comprise electrospun polymer fibers embedded with the ceramic material comprising porous ceramic granules.

9. The composition of claim 8, wherein the porous ceramic granules have an average diameter from about 50 μm to 800 μm and comprise hydroxyapatite and beta-tricalcium phosphate.

10. The composition of claim 5, wherein the fluid comprises bone marrow aspirate, saline, sterile water, blood for injection, phosphate buffered saline, dextrose, Ringer's lactated solution, or a combination thereof.

11. The composition of claim 5, wherein the ratio of fluid to the plurality of lyophilized porous macroparticles is from about 0.5:1 to about 3:1.

12. A uniformly hydrated composition made by the method of claim 1, the uniformly hydrated composition comprising a plurality of lyophilized porous macroparticles comprising porous ceramic granules having an average diameter from about 50 µm to 800 µm and in an amount from about 50 to about 98 wt. % and collagen in an amount from about 2 to about 50 wt. % based on a total weight of each of the lyophilized porous macroparticles, the ceramic granules comprising hydroxyapatite and beta-tricalcium phosphate having a calcium to phosphate ratio of between 1.0 to about 2.0, the ceramic granules are in the form of macroparticles having an average diameter from about 4 mm to about 6 mm and a density of 0.1 to 0.6 g/cc, each of the lyophilized porous macroparticles having an average diameter from about 0.1 mm to about 10 mm.

13. The composition of claim 12, wherein each of the porous ceramic granules comprise an outer surface comprising a plurality of concave shapes each having a diameter of from about 400 to about 600 microns.

14. The composition of claim 12, wherein each of the porous ceramic granules have a microporosity, and the diameter of each of the micropores is from about 0.01 to about 10 microns.

15. The composition of claim 12, wherein the plurality of lyophilized porous macroparticles has shapes comprising cylinders, cubes, rods, tubes, hollow tubes, rectangles, discs, half hemispherical hollow tubes, electrospun fibers, or a combination thereof.

16. The method of claim 1, wherein the macroparticles to the open space in the chamber has a volume ratio of about 1:1.

* * * * *